(12) United States Patent
Kang

(10) Patent No.: US 11,141,057 B2
(45) Date of Patent: Oct. 12, 2021

(54) METHOD AND APPARATUS FOR DETERMINING METAMORPHOPSIA BASED ON USER INTERACTION

(71) Applicant: Samsung Life Public Welfare Foundation, Seoul (KR)

(72) Inventor: Se Woong Kang, Seongnam-si (KR)

(73) Assignee: SAMSUNG LIFE PUBLIC WELFARE FOUNDATION

(*) Notice: Subject to any disclaimer, the term of this patent is extended or adjusted under 35 U.S.C. 154(b) by 280 days.

(21) Appl. No.: 16/340,942

(22) PCT Filed: Sep. 29, 2017

(86) PCT No.: PCT/KR2017/011048
§ 371 (c)(1),
(2) Date: Apr. 10, 2019

(87) PCT Pub. No.: WO2018/070736
PCT Pub. Date: Apr. 19, 2018

(65) Prior Publication Data
US 2019/0231186 A1    Aug. 1, 2019

(30) Foreign Application Priority Data

Oct. 11, 2016 (KR) .................. 10-2016-0131376
Sep. 29, 2017 (KR) .................. 10-2017-0127591

(51) Int. Cl.
*A61B 3/00*    (2006.01)
*A61B 3/032*   (2006.01)
(Continued)

(52) U.S. Cl.
CPC .......... *A61B 3/0033* (2013.01); *A61B 3/0016* (2013.01); *A61B 3/0041* (2013.01);
(Continued)

(58) Field of Classification Search
CPC ... A61B 3/0016; A61B 3/0033; A61B 3/0075; A61B 3/032; A61B 3/0041; A61B 3/0058; A61B 3/02; A61B 3/024; A61B 3/18

See application file for complete search history.

(56) References Cited

U.S. PATENT DOCUMENTS

| | | | |
|---|---|---|---|
| 4,798,456 A | * | 1/1989 | Enoch .................. A61B 3/1176 351/222 |
| 5,892,570 A | | 4/1999 | Stevens |

(Continued)

FOREIGN PATENT DOCUMENTS

| | | |
|---|---|---|
| GB | 2457735 A | 8/2009 |
| JP | 2001149314 | 6/2001 |

(Continued)

OTHER PUBLICATIONS

Extended European Search Report corresponding to EP 17860716.4; dated Jul. 6, 2020 (9 pages).

(Continued)

*Primary Examiner* — Jordan M Schwartz
(74) *Attorney, Agent, or Firm* — Myers Bigel, P.A.

(57) ABSTRACT

According to a method for determining metamorphopsia based on user interaction disclosed as an embodiment of the present invention, a test chart may be displayed to a user, an input from the user for a part which is perceived as being distorted in the displayed test chart may be received, and a metamorphopsia degree of the user may be accurately determined based on a distortion area selected according to the received input. Further, according to another embodiment of the present invention, a test chart may be displayed to a user, a response (e.g., distance values of points, an area value, etc. in a zone) for each zone for the test chart may be (Continued)

received from the user, and metamorphopsia of the user may be determined based on the received response.

20 Claims, 10 Drawing Sheets

(51) Int. Cl.
    *A61B 3/024*    (2006.01)
    *A61B 3/18*    (2006.01)
    *A61B 3/02*    (2006.01)

(52) U.S. Cl.
    CPC .............. *A61B 3/0075* (2013.01); *A61B 3/02* (2013.01); *A61B 3/024* (2013.01); *A61B 3/032* (2013.01); *A61B 3/18* (2013.01)

(56) References Cited

U.S. PATENT DOCUMENTS

| | | |
|---|---|---|
| 6,585,376 B1 | 7/2003 | Matsumoto |
| 8,047,652 B1 | 11/2011 | Collazo |
| 9,131,838 B1 * | 9/2015 | Bruun-Jensen ........ A61B 3/024 |
| 2015/0201832 A1 | 7/2015 | Palanker |
| 2016/0235291 A1 | 8/2016 | Goh et al. |
| 2018/0235459 A1 * | 8/2018 | Claessens ............... G06F 3/013 |

FOREIGN PATENT DOCUMENTS

| | | |
|---|---|---|
| JP | 3320060 B2 | 9/2002 |
| JP | 2003265412 | 9/2003 |
| JP | 5436712 B1 | 12/2013 |
| KR | 1020150111621 | 10/2015 |
| WO | 2014024700 A1 | 2/2014 |

OTHER PUBLICATIONS

International Search Report corresponding to International Patent Application No. PCT/KR2017/011048, dated Apr. 24, 2018. (5 pages with English translation).

\* cited by examiner

METHOD AND APPARATUS FOR DETERMINING METAMORPHOPSIA BASED ON USER INTERACTION

CROSS REFERENCE TO RELATED APPLICATIONS

This application is a 35 U.S.C. § 371 national stage application of PCT International Application No. PCT/KR2017/011048, filed Sep. 29, 2017, which claims priority from Korean Patent Application No. 10-2017-0127591, filed Sep. 29, 2017, and Korean Patent Application No. 10-2016-0131376, filed on Oct. 11, 2016, the contents of which are incorporated herein in their entireties by reference. The above-referenced PCT International Application was published in the Korean language as International Publication No. WO 2018/070736 A2 on Apr. 19, 2018.

TECHNICAL FIELD

The present invention relates to a method and an apparatus for determining metamorphopsia based on user interaction, and more particularly, to a method and an apparatus for determining metamorphopsia for classifying and indicating a degree of metamorphopsia based on an area of a metamorphopsia region according to a user input inputted with respect to a test chart.

BACKGROUND ART

Metamorphopsia refers to a state in which an object appears distorted or deformed. In other words, the metamorphopsia refers to a symptom in which a straight-line plaid pattern appears warped in a wave shape or crumpled and distorted.

The metamorphopsia may be caused by diseases such as macular surface abnormalities of the macula choroid, such as macular hole in the epiretinal membrane as well as macular degeneration or central serous chorioretinopathy. In other words, the eye's structure, which acts as a film of a camera, that is, an image is focused on the eye, is the retina, and in the retina, if abnormalities occur in the macula, which accounts for a central view function of 90% or more in the retina, the metamorphopsia may be caused. In some diseases, the degree of the metamorphopsia is more closely related to quality of life (QOL) than to vision.

As a measurement index of the metamorphopsia in the related art, an Amsler grid has often been used. When a checkered pattern of a regular distance is observed with a lesion of the eye, the above-mentioned symptom (for example, the metamorphopsia symptom such as the appearance of a bent or obscured streak may occur when the macular abnormality is present. However, metamorphopsia measurement using the Amsler grid in the related art has a problem that a distance between lines of the Amsler grid is fixedly determined in advance and a patient has his/her own metamorphopsia but can not quantify the degree of incidence of the metamorphopsia. On the other hand, a metamorphopsia chart (M-CHART) has been used as one of the measurement indexes of the metamorphopsia in the related art. The M-CHART which has a shape in which a point distance gradually increases at a visual angle of 0.2 to 2.0 degrees (e.g., a distance of 0.1 degree) is generally constituted by a total of 19 dotted lines. In a case where there is the metamorphopsia, when the point distance gradually increases, the dotted line will be warped and not seen at any moment, and the visual angle immediately therebefore will be evaluated as an M-score. Although quantitative assessment of the degree of metamorphopsia is possible to some degree through the M-CHART, only the degree of metamorphopsia of a center is measured, and as a result, there is still a problem in that a metamorphopsia occurrence range of an external viewing field which is out of the center cannot be reflected.

DETAILED DESCRIPTION OF THE INVENTION

Technical Problem

The present invention is directed to providing an example of a method and an apparatus for determining metamorphopsia based on user interaction, and when a method and an apparatus according to an embodiment of the present invention are used, it is possible to display a test chart to a user, receive an input from the user for a portion that is perceived as being distorted in the displayed test chart, and accurately determine a degree of metamorphopsia of the user based on a selected distortion area according to the received input.

Further, according to another embodiment of the present invention, it is possible to display a test chart for a user, receive a response (e.g., an area value of a region in which metamorphopsia is perceived and a distance value of points when the metamorphopsia may not be perceived any longer in the region) for each zone for the test chart from the user, and accurately determine a range and a degree of the metamorphopsia of the user based on the received response.

Technical Solution

As an embodiment of the present invention, a method and an apparatus for determining metamorphopsia based on user interaction may be provided.

A method for determining metamorphopsia based on user interaction according to an embodiment of the present invention may include displaying a test chart to a user; receiving a user display input for displaying at least one metamorphopsia region with respect to the displayed test chart; displaying the test chart, while adjusting distances of a plurality of points in at least one metamorphopsia region displayed based on the received user display input by a point distance adjustment signal applied from the user; and acquiring a distance value of a plurality of points in the at least one metamorphopsia region and an area value of the metamorphopsia region when it is selected by the user that the metamorphopsia is not perceived, repeatedly performing the previous steps when a user input that the metamorphopsia region still exists is received by the user in a display part other than at least one metamorphopsia region displayed, and determining the metamorphopsia of the user based on the acquired distance of the points and area value when the metamorphopsia region does not exist any longer on the test chart.

The test chart according to an embodiment of the present invention may be a polygonal or circular grid and a user display input for displaying at least one metamorphopsia region for the test chart may be received through a user input unit of a metamorphopsia determining apparatus and the user display input may form a closed line on the test chart.

A center point having a predetermined size may be displayed on the test chart having a grid shape with respect to a visual angle of the user.

The test chart may be displayed as a black grid on a white background or as a white grid on a black background.

A metamorphopsia degree of the user may be determined by a multiplication result value of the acquired distance value of points and area value, by a value obtained by subtracting the multiplication result value from a measurement reference value, or by a multiplication result value of a ratio value of the acquired distance of the points to a distance between respective lines and the acquired area value in the test chart having the grid shape. In other words, a scheme of calculating a result value may be diversified. For example, (i) the numerical value itself obtained by multiplying the point distance value and the area value may be directly used as the result value or (ii) a value obtained by subtracting the value obtained by multiplying the point distance value, the area value, etc., from a reference value (e.g., 100) may be used for determining the metamorphopsia as the result value. Further, (iii) a grade may be predetermined according to a predetermined reference and the result value may be represented to correspond to a predetermined grade range and used for determining the metamorphopsia. For example, a grade range may be preset so that in a case where the result value is more than 0 and 10 or less, the case is classified to grade 1 and in a case where the result value is 11 or more and 20 or less, the case is classified to grade 2, etc., and a result may be represented by a step to which the result value obtained by multiplying the point distance value and the area value belongs to determine the metamorphopsia degree. Further, (iv) the point distance value and the area value may be classified and expressed in grades from the beginning and the result value may be represented. For example, the point distance value may be divided into steps 1 to 14 and the area value may be divided into steps 14 of A to N and then, the result value may be represented by 2B, 5F, 14D, etc. In addition, various combination examples described above may be also divided into the grades and expressed. Further, (v) the metamorphopsia may be determined by the multiplication result value of the ratio value of the distance of points acquired to the distance of respective lines and the acquired area value in the grid-shaped test chart. In addition, (vi) in the aforementioned example, according to a predetermined zone with respect to the point distance value and the area value, the result value may be obtained by assigning a predetermined weight to each value (e.g., the point distance value, the area value, etc.) as being closer to the center.

Further, an apparatus for determining metamorphopsia based on user interaction according to an embodiment of the present invention may include a display unit for displaying a test chart to a user; a user input receiving unit receiving a user display input for displaying at least one metamorphopsia region with respect to the test chart displayed through the display unit; a point distance adjusting unit for adjusting distances of a plurality of points in at least one metamorphopsia region displayed based on the user display input received by the user input receiving unit by a point distance adjustment signal applied from the user; a test information acquiring unit for acquiring distance values of a plurality of points within at least one metamorphopsia region and an area value of the metamorphopsia region when it is selected that the metamorphopsia is not perceived by the user; and a metamorphopsia determining unit repeatedly performing previous steps when a user input that the metamorphopsia region still exists in a display part other than at least one metamorphopsia region displayed is received by the user and determining the metamorphopsia of the user based on the distance values of the points and the area value acquired by the test information acquiring unit when the metamorphopsia region does not exist on the test chart any longer.

A method for determining metamorphopsia based on user interaction according to another embodiment of the present invention may include displaying a test chart to a user; receiving a user display input for displaying at least one metamorphopsia region with respect to the displayed test chart; displaying a metamorphopsia region on the test chart for each zone based on the received user display input; receiving a user adjustment input for adjusting distances of a plurality of points in a region until the metamorphopsia is not perceived with respect to the metamorphopsia region included in a displayed first zone to be selected by the user; acquiring distance values of a plurality of points within the region and an area value of the metamorphopsia region when it is selected that the metamorphopsia is not perceived by the user; receiving the user adjustment input and acquiring each of the distance values of the plurality of points and the area value of the metamorphopsia region for each zone for zones other than Zone 1 above; and displaying the test chart including the zone in which the distances of the points are adjusted, repeatedly performing previous steps when a user input that the metamorphopsia region still exists is received by the user, and quantitatively determining the metamorphopsia by reflecting a weight for each zone based on the acquired distance values of the points and area value when the metamorphopsia region does not exist. In the test chart according to an embodiment of the present invention, a plurality of concentric circle-shaped zones having different sizes may exist around a center point and a concentric circle indicating each zone may have a diameter corresponding to a visual angle of the user from the center point.

Further, according to an embodiment of the present invention, the user may increase or decrease the distances of the plurality of points based on the user adjustment input and the distances of the plurality of points may be fixed according to selection (e.g., clicking a button or an icon) of an absence time (e.g., a time when the user determines that the metamorphopsia does not exist in a given region) of the metamorphopsia in the region by the user and the area value of the region where the metamorphopsia is perceived and the distance values of the plurality of points at the absence time of the metamorphopsia may be acquired.

According to an embodiment of the present invention, in a state where a plurality of points of a fixed distance at the time selected by the user for the region where the metamorphopsia is perceived, which is included in Zone 1 is displayed together with a plurality of points in a region where the metamorphopsia is perceived, which is included in Zone 2, the distances of the plurality of points in the region where the metamorphopsia is perceived, which is included in Zone 2 increase or decrease based on the received user adjustment input and the distances of the plurality of points in Zone 2 are fixed by the selection of the absence time of the metamorphopsia in the region within Zone 2 by the user, and the area value of the region where the metamorphopsia is perceived, which is included in Zone 2 and the distance values of the plurality of points in Zone 2 at the absence time of the metamorphopsia may be acquired.

Further, according to an embodiment of the present invention, in a state where the plurality of points of the fixed distance in Zone 1 and the plurality of points of the fixed distance in Zone 2 are displayed together with the plurality of points in the region where the metamorphopsia is perceived, which is included in Zone 3, the distances of the plurality of points in the region where the metamorphopsia is perceived, which is included in Zone 3 increase or decrease based on the received user adjustment input and the distances of the plurality of points in Zone 3 are fixed by the selection of the absence time of the metamorphopsia in the region within Zone 3 by the user, and the area value of the region where the metamorphopsia is perceived, which is included in Zone 3 and the distance values of the plurality of points in Zone 3 at the absence time of the metamorphopsia may be acquired.

Further, according to an embodiment of the present invention, the entirety of the test chart including the plurality of points where the distances of the points are adjusted up to the time when the metamorphopsia is not perceived by the user adjustment input for each zone of the metamorphopsia region is displayed and when the region where the metamorphopsia is perceived does not exist in the test chart any longer, the metamorphopsia degree of the user may be determined based on the area value and the distances of the points of the metamorphopsia region for each zone.

According to an embodiment of the present invention, the metamorphopsia degree of the user may be determined based on a difference between the total length of a solid line included in the first test chart before a metamorphopsia test for the user and the total sum of the distances of the points for each zone.

Further, according to an embodiment of the present invention, a weight is differently applied for each zone to correct the total sum of the distances of the points and the weight may be assigned to be high as being closer to the center of the test chart.

An apparatus for determining metamorphopsia based on user interaction according to another embodiment of the present invention may include a display unit for displaying a test chart to a user; a user input receiving unit receiving a user display input for displaying at least one metamorphopsia region with respect to the test chart displayed through the display unit; a test information acquiring unit for acquiring distance values of a plurality of points in a region and an area value of the metamorphopsia region when the region where the metamorphopsia is perceived in the test chart is displayed for each zone through the display unit based on the user display input received through the user input receiving unit, a user adjustment input for adjusting the distances of the plurality of points is received through the user input receiving unit until it is selected by the user that the metamorphopsia is not perceived with respect to a metamorphopsia region included in displayed Zone 1, in which when the user adjustment input is received for zones other than Zone 1 above and each of the distance values of the plurality of points and the area value of the region where the metamorphopsia is perceived for each zone is acquired, and a test chart including a zone where the distances of the points are adjusted is displayed through the display unit, and a message that the metamorphopsia region still exists is received through the user input receiving unit by the user, addition of display of metamorphopsia region and adjustment of the distances of the plurality of points in the region for each zone may be repeatedly performed. The apparatus may include a metamorphopsia determining unit for determining a range and a degree (e.g., a grade or a representative value) of the metamorphopsia to which a weight for each zone is reflected based on an area value of the metamorphopsia region for each zone and distance values of the points at a time when the metamorphopsia is not perceived any longer.

Meanwhile, as an embodiment of the present invention, a computer readable recording medium having a program for executing the aforementioned method in a computer, which is recorded therein may be provided.

Advantageous Effects

When a method and an apparatus for determining metamorphopsia based on user interaction are used, not only a degree of warping of a test chart in a central visual field but also a peripheral vision can be tested. In other words, it is possible to test the degree of the metamorphopsia for the entire visual field of a patient and a test to which a state of the patient is more actively reflected can be performed in that such a test can be performed based on patient's selection. A quantitative evaluation can be achieved in that the patient autonomously draws and marks a region where a visual field distortion occurs on a grid and a degree of deformation according to an area and a distance value between points of a region (e.g., a deformation view region) which is perceived as being distorted by the patient can be tested with respect to the entire visual field of the patient or a degree thereof can be quantified and measured.

Further, according to an embodiment of the present invention, it is possible to quantitatively evaluate an incidence range and an incidence degree of the metamorphopsia which is important in a quality of life for a patient having a macular abnormality. In other words, by using the method and apparatus according to an embodiment of the present invention, it is possible to simultaneously evaluate and determine the incidence range and the incidence degree of the metamorphopsia (e.g., a progress level of a disease).

BEST MODE

Figure 1:
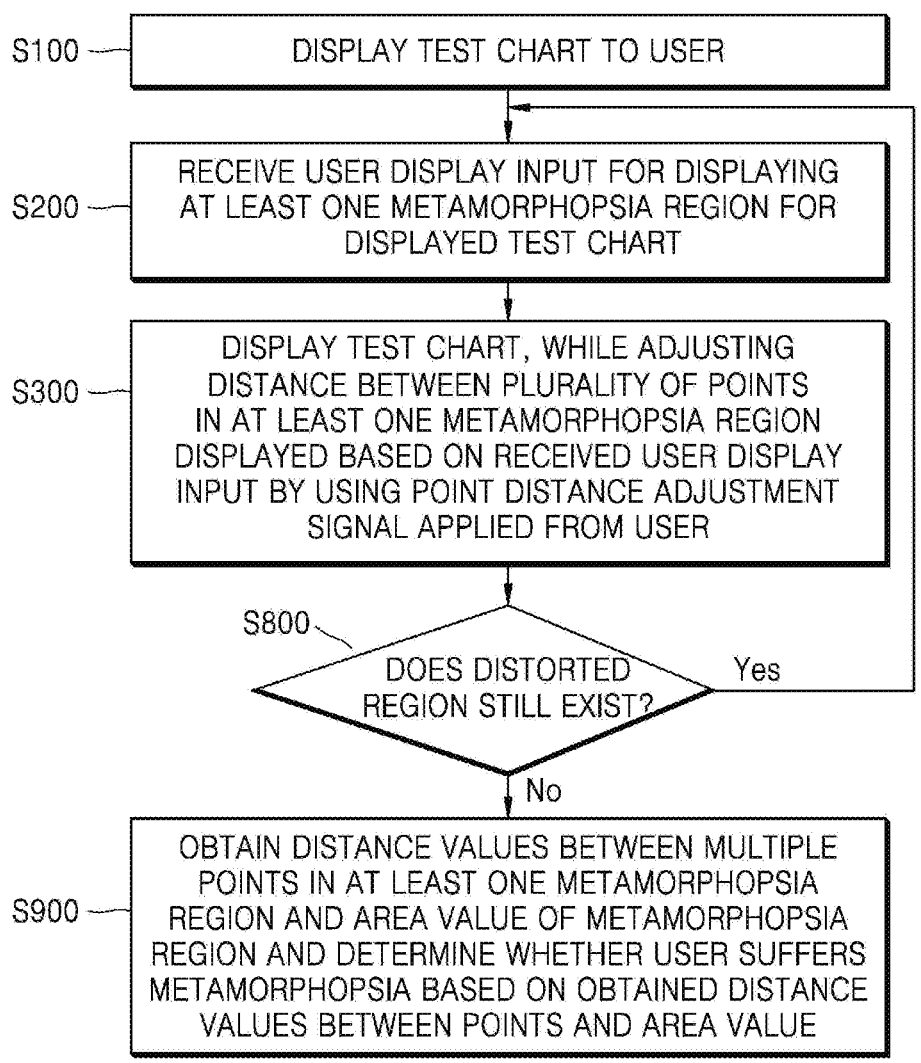
FIG. 1 is a flowchart illustrating a method for determining metamorphopsia using a point distance and an area based on user interaction according to an embodiment of the present invention.

A method for determining metamorphopsia based on user interaction according to an embodiment of the present invention may include displaying a test chart to a user; receiving a user display input for displaying at least one metamorphopsia region with respect to the displayed test chart; displaying the test chart, while adjusting distances of a plurality of points in at least one metamorphopsia region displayed based on the received user display input by a point distance adjustment signal applied from the user; and acquiring a distance value of a plurality of points in the at least one metamorphopsia region and an area value of the metamorphopsia region when it is selected by the user that the metamorphopsia is not perceived, repeatedly performing the previous steps when a user input that the metamorphopsia region still exists is received by the user in a display part other than at least one metamorphopsia region displayed, and determining the metamorphopsia of the user based on the acquired distance values of the points and area value when the metamorphopsia region does not exist any longer on the test chart.

The test chart according to an embodiment of the present invention may be a polygonal or circular grid and a user display input for displaying at least one metamorphopsia region for the test chart may be received through a user input unit of a metamorphopsia determining apparatus and the user display input may form a closed line on the test chart.

A center point having a predetermined size may be displayed on the test chart having a grid shape with respect to a visual angle of the user.

The test chart may be displayed as a black grid on a white background or as a white grid on a black background.

A metamorphopsia degree of the user may be determined by a multiplication result value of the acquired distance value of points and area value, by a value obtained by subtracting the multiplication result value from a measurement reference value, or by a multiplication result value of a ratio value of the acquired distance of the points to a distance between respective lines and the acquired area value in the test chart having the grid shape. In other words, a scheme of calculating a result value may be diversified. For example, (i) the numerical value itself obtained by multiplying the point distance value and the area value may be directly used as the result value or (ii) a value obtained by subtracting the value obtained by multiplying the point distance value, the area value, etc., from a reference value (e.g., 100) may be used for determining the metamorphopsia as the result value. Further, a grade is predetermined according to a predetermined reference and the result value is represented to correspond to a predetermined grade range to be used for determining the metamorphopsia. For example, a grade range may be preset so that in a case where the result value is more than 0 and 10 or less, the case is classified to grade 1 and in a case where the result value is 11 or more and 20 or less, the case is classified to grade 2, etc., and a result is represented by a step to which the result value obtained by multiplying the point distance value and the area value belongs to determine the metamorphopsia degree. Further, (iv) the point distance value and the area value may be classified and expressed in grades from the beginning and the result value may be represented. For example, the point distance value may be divided into steps 1 to 14 and the area value may be divided into steps 14 of A to N and then, the result value may be represented by 2B, 5F, 14D, etc. In addition, various combination examples described above may also be divided into the grades and expressed. Further, (v) the metamorphopsia may be determined by the multiplication result value of the ratio value of the distance of points acquired to the distance of respective lines and the acquired area value in the grid-shaped test chart. In addition, (vi) in the aforementioned example, according to a predetermined zone with respect to the point distance value and the area value, the result value may be obtained by assigning a predetermined weight to each value (e.g., the point distance value, the area value, etc.) as being closer to the center.

Further, an apparatus for determining metamorphopsia based on user interaction according to an embodiment of the present invention may include a display unit for displaying a test chart to a user; a user input receiving unit receiving a user display input for displaying at least one metamorphopsia region with respect to the test chart displayed through the display unit; a point distance adjusting unit for adjusting distances of a plurality of points in at least one metamorphopsia region displayed based on the user display input received by the user input receiving unit by a point distance adjustment signal applied from the user; a test information acquiring unit for acquiring distance values of a plurality of points within at least one metamorphopsia region and an area value of the metamorphopsia region when it is selected that the metamorphopsia is not perceived by the user; and a metamorphopsia determining unit repeatedly performing previous steps when a user input that the metamorphopsia region still exists in a display part other than at least one metamorphopsia region displayed is received by the user and determining the metamorphopsia of the user based on the distance values of the points and the area value acquired by the test information acquiring unit when the metamorphopsia region does not exist on the test chart any longer.

A method for determining metamorphopsia based on user interaction according to another embodiment of the present invention may include displaying a test chart to a user; receiving a user display input for displaying at least one metamorphopsia region on the displayed test chart; displaying a metamorphopsia region on the test chart for each zone based on the received user display input; receiving a user adjustment input for adjusting distances of a plurality of points in a region until it is selected by the user that the metamorphopsia is not perceived with respect to the metamorphopsia region included in a displayed first zone; acquiring distance values of a plurality of points within the region and an area value of the metamorphopsia region when it is selected that the metamorphopsia is not perceived by the user; receiving the user adjustment input and acquiring each of the distance values of the plurality of points and the area value of the metamorphopsia region for each zone for zones other than Zone 1 above; and displaying the test chart including the zone in which the distances of the points are adjusted, repeatedly performing previous steps when a user input that the metamorphopsia region still exists is received by the user, and quantitatively determining the metamorphopsia by reflecting a weight for each zone based on the acquired distance values of the points and area value when the metamorphopsia region does not exist. In the test chart according to an embodiment of the present invention, a plurality of concentric circle-shaped zones having different sizes may exist around a center point and a concentric circle indicating each zone may have a diameter corresponding to a visual angle of the user from the center point.

Further, according to an embodiment of the present invention, the user may increase or decrease the distances of the plurality of points by the user adjustment input of the user and the distances of the plurality of points are fixed according to selection (e.g., clicking a button or an icon) of an absence time (e.g., a time when the user determines that the metamorphopsia does not exist in a given region) of the metamorphopsia in the region by the user and the area value of the region where the metamorphopsia is perceived and the distance values of the plurality of points at the absence time of the metamorphopsia may be acquired.

According to an embodiment of the present invention, in a state where a plurality of points of a fixed distance at the time selected by the user for the region where the metamorphopsia is perceived, which is included in Zone 1 is selected by the user is displayed together with a plurality of points in a region where the metamorphopsia is perceived, which is included in Zone 2, the distances of the plurality of points in the region where the metamorphopsia is perceived, which is included in Zone 2 increase or decrease based on the received user adjustment input and the distances of the plurality of points in Zone 2 are fixed by the selection of the absence time of the metamorphopsia in the region within Zone 2 by the user, and the area value of the region where the metamorphopsia is perceived in Zone 2 and the distance values of the plurality of points in Zone 2 at the absence time of the metamorphopsia may be acquired.

Further, according to an embodiment of the present invention, in a state where the plurality of points of the fixed distance in Zone 1 and the plurality of points of the fixed distance in Zone 2 are displayed together with the plurality of points in the region where the metamorphopsia is perceived, which is included in Zone 3, the distances of the plurality of points in the region where the metamorphopsia is perceived, which is included in Zone 3 increase or decrease based on the received user adjustment input and the distances of the plurality of points in Zone 3 are fixed by the selection of the absence time of the metamorphopsia in the region within Zone 3 by the user, and the area value of the region where the metamorphopsia is perceived in Zone 3 and the distance values of the plurality of points in Zone 3 at the absence time of the metamorphopsia may be acquired.

Further, according to an embodiment of the present invention, the entirety of the test chart including the plurality of points where the distances of the points are adjusted up to the time when the metamorphopsia is not perceived by the user adjustment input for each zone of the metamorphopsia region is displayed and when the region where the metamorphopsia is perceived does not exist in the test chart any longer, the metamorphopsia degree of the user may be determined based on the area value and the distances of the points of the metamorphopsia region for each zone.

According to an embodiment of the present invention, the metamorphopsia degree of the user may be determined based on a difference between the total length of a solid line included in the first test chart before a metamorphopsia test for the user and the total sum of the distances of the points for each zone.

Further, according to an embodiment of the present invention, a weight is differently applied for each zone to correct the total sum of the distances of the points and a higher weight may be assigned to a zone which is closer to the center of the test chart.

An apparatus for determining metamorphopsia based on user interaction according to another embodiment of the present invention may include a display unit for displaying a test chart to a user; a user input receiving unit receiving a user display input for displaying at least one metamorphopsia region with respect to the test chart displayed through the display unit; and a test information acquiring unit for acquiring distance values of a plurality of points in a region and an area value of the corresponding region when the region where the metamorphopsia is perceived in the test chart is displayed for each zone through the display unit based on the user display input received through the user input receiving unit, a user adjustment input for adjusting the distances of the plurality of points is received through the user input receiving unit until it is selected by the user that the metamorphopsia is not perceived with respect to a region where the metamorphopsia is perceived, which is included in displayed Zone 1, and it is selected by the user that the metamorphopsia is not perceived, in which when the user adjustment input is received for zones other than Zone 1 above and each of the distance values of the plurality of points and the area value of the region where the metamorphopsia is perceived for each zone is acquired, and a test chart including a zone where the distances of the points are adjusted is displayed through the display unit, and when a message that the metamorphopsia region still exists is received through the user input receiving unit by the user, addition of display of a metamorphopsia region and adjustment of the distances of the plurality of points in the region for each zone may be repeatedly performed. The apparatus may include a metamorphopsia determining unit for determining a range and a degree (e.g., a grade or a representative value) of the metamorphopsia to which a weight for each zone is reflected based on an area value of the metamorphopsia region for each zone and distance values of the points at a time when the metamorphopsia is not perceived any longer.

Meanwhile, as an embodiment of the present invention, a computer readable recording medium having a program for executing the aforementioned method in a computer, which is recorded therein may be provided.

[Mode for Invention]

Hereinafter, embodiments of the present invention will be described in detail so as to be easily implemented by those skilled in the art, with reference to the accompanying drawings. However, the present invention may be implemented in various different forms and is not limited to an embodiment described herein. In addition, a part not related with a description is omitted in order to clearly describe the present invention in the drawings and throughout the specification, like reference numerals designate like elements.

Terms used in the present specification will be described in brief and the present invention will be described in detail.

Terms used in the present invention adopt general terms which are currently widely used as possible by considering functions in the present invention, but the terms may be changed depending on an intention of those skilled in the art, a precedent, emergence of new technology, etc. Further, in a specific case, a term which an applicant arbitrarily selects is present and in this case, a meaning of the term will be disclosed in detail in a corresponding description part of the invention. Accordingly, a term used in the present invention should be defined based on not just a name of the term but a meaning of the term and contents throughout the present invention.

Further, throughout the specification, unless explicitly described to the contrary, the word "comprise" and variations such as "comprises" or "comprising", will be understood to imply the inclusion of stated elements but not the exclusion of any other elements. In addition, terms including "part", "module", and the like disclosed in the specification mean a unit that processes at least one function or operation and this may be implemented by hardware or software or a combination of hardware and software. Further, throughout the specification, when it is described that a part is "connected" with another part, it means that the certain part may be "directly connected" with the another part and a third part may be interposed therebetween as well.

Hereinafter, the present invention will be described in detail with reference to the accompanying drawings.

FIG. 1 is a flowchart illustrating a method for determining metamorphopsia using a point distance and an area based on user interaction according to an embodiment of the present invention.

A method for determining metamorphopsia based on user interaction according to an embodiment of the present invention may include displaying a test chart for a user (S100), receiving a user display input for displaying at least one metamorphopsia region with respect to the displayed test chart (S200), displaying the test chart, while adjusting distances of a plurality of points in at least one metamorphopsia region displayed based on the received user display input by a point distance adjustment signal applied from the user (S300), determining whether a distorted region still exists (S800), and acquiring a distance value of a plurality of points in at least one metamorphopsia region and an area value of the metamorphopsia region when it is selected that the metamorphopsia is not perceived by the user and determining the metamorphopsia of the user based on the acquired distance value of the points and the acquired area value (S900). Further, when a user input that the metamorphopsia region still exists is received by the user in a display part other than at least one metamorphopsia region displayed, the previous steps (S200 to S300) are repeatedly performed while the previously displayed metamorphopsia region is shown and when the metamorphopsia region does not exist on the test chart any longer, the distance value of the plurality of points within at least one metamorphopsia region and an area value of the metamorphopsia region may be acquired and the metamorphopsia of the user may be determined based on the acquired distance value of points and the acquired area value (S900).

In a method for testing metamorphopsia according to an embodiment of the present invention, the test chart is displayed to the user, the user is allowed to display a region in which a line is perceived as being distorted, the distances of the points within the display region are gradually adjusted and it is perceived that there is no distortion in the region displayed by the user and a primary test may be completed when a stop (end) of adjustment of a point distance is selected. When the primary test is completed and then, another part in which the line is perceived as being distorted additionally exists, the test may be repeated while the point distance is gradually adjusted after both the existing displayed region and a new displayed region are displayed again (e.g., a secondary test, etc.). According to such a test scheme, the degree of deformation in a peripheral view as well as a central visual field of the user may be effectively tested (determined).

According to an embodiment of the present invention, the distances of the plurality of points may be simultaneously adjusted within the displayed metamorphopsia region.

A metamorphopsia degree of the user may be determined by a multiplication result value of the distance value of points and the area value which are acquired. The distances of the points, etc. will be described below. For example, when the metamorphopsia degree is determined by the multiplication result value of the distance value of the points and the area value, it is meant that an eye state of the user (patient) is worse as a numerical value is larger.

Further, contrary to the above case, the metamorphopsia degree may be determined by a value obtained by subtracting the multiplication result value from a measurement reference value (e.g., 100, etc.). Such a determination scheme may mean that the eye state of the patient is better as a subtraction result value is larger similarly to vision measurement in the related art.

Further, the metamorphopsia degree may be determined by a multiplication result value of a ratio value of a distance (d) of points acquired to a distance (g) of respective lines and the acquired area value in a grid-shaped test chart 10. In other words, the metamorphopsia degree of the patient may be determined based on a metamorphopsia incidence region to which a grid density is reflected. As the grid density decreases (e.g., when the distances of the respective lines are larger), the distance ratio value (d/g) of the points relatively increases, and as a result, the multiplication result value may be represented to be large. In such a case, it may be meant that as a numerical value of the multiplication result value is larger, the eye state of the user (patient) is worse.

According to an embodiment of the present invention, a scheme of calculating a result value may be diversified. For example, as described above, (i) the numerical value itself obtained by multiplying the point distance value and the area value may be directly used as the result value or (ii) a value obtained by subtracting the value obtained by multiplying the point distance value, the area value, etc., from a reference value (e.g., 100) may be used for determining the metamorphopsia as the result value. Further, (iii) a grade is predetermined according to a predetermined reference and the result value is represented to correspond to a range of the predetermined grade to be used for determining the metamorphopsia. For example, a grade range may be preset so that in a case where the result value is more than 0 and 10 or less, the case is classified to grade 1 and in a case where the result value is 11 or more and 20 or less, the case is classified to grade 2, etc., and a result is represented by a step to which the result value obtained by multiplying the point distance value and the area value belongs to determine the metamorphopsia degree. Further, (iv) the point distance value and the area value may be classified and expressed in grades from the beginning and the result value may be represented. For example, the point distance value may be divided into grades 1 to 14 and the area value may be divided into 14 grades of A to N and then, the result value may be represented by 2B, 5F, 14D, etc. In addition, various combination examples described above may be also divided into the grades and expressed. Further, (v) the metamorphopsia may be determined by the multiplication result value of the ratio value of the distance of points acquired to the distance of respective lines and the acquired area value in the grid-shaped test chart. In addition, (vi) in the aforementioned example, according to a predetermined zone with respect to the point distance value and the area value, the result value may be obtained by assigning a predetermined weight to each value (e.g., the point distance value, the area value, etc.) as being closer to the center.

Figure 2A:
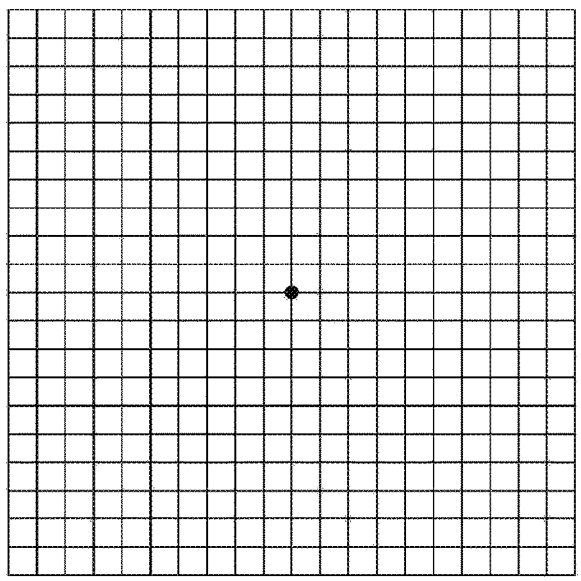
FIG. 2 illustrates an example of a test chart according to an embodiment of the present invention.
Figure 2B:
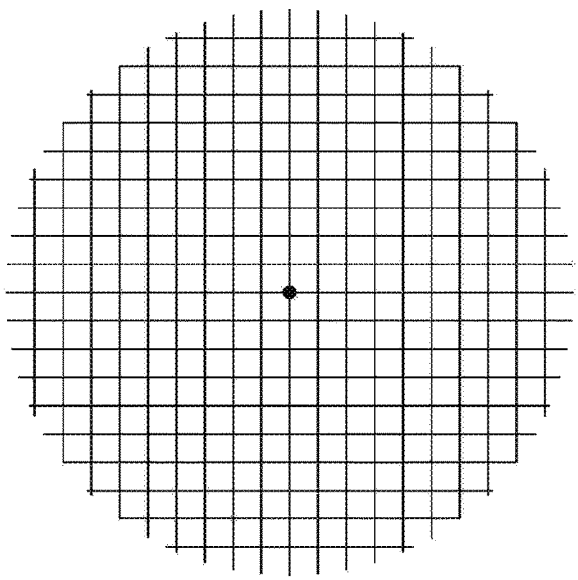
Figure 3:
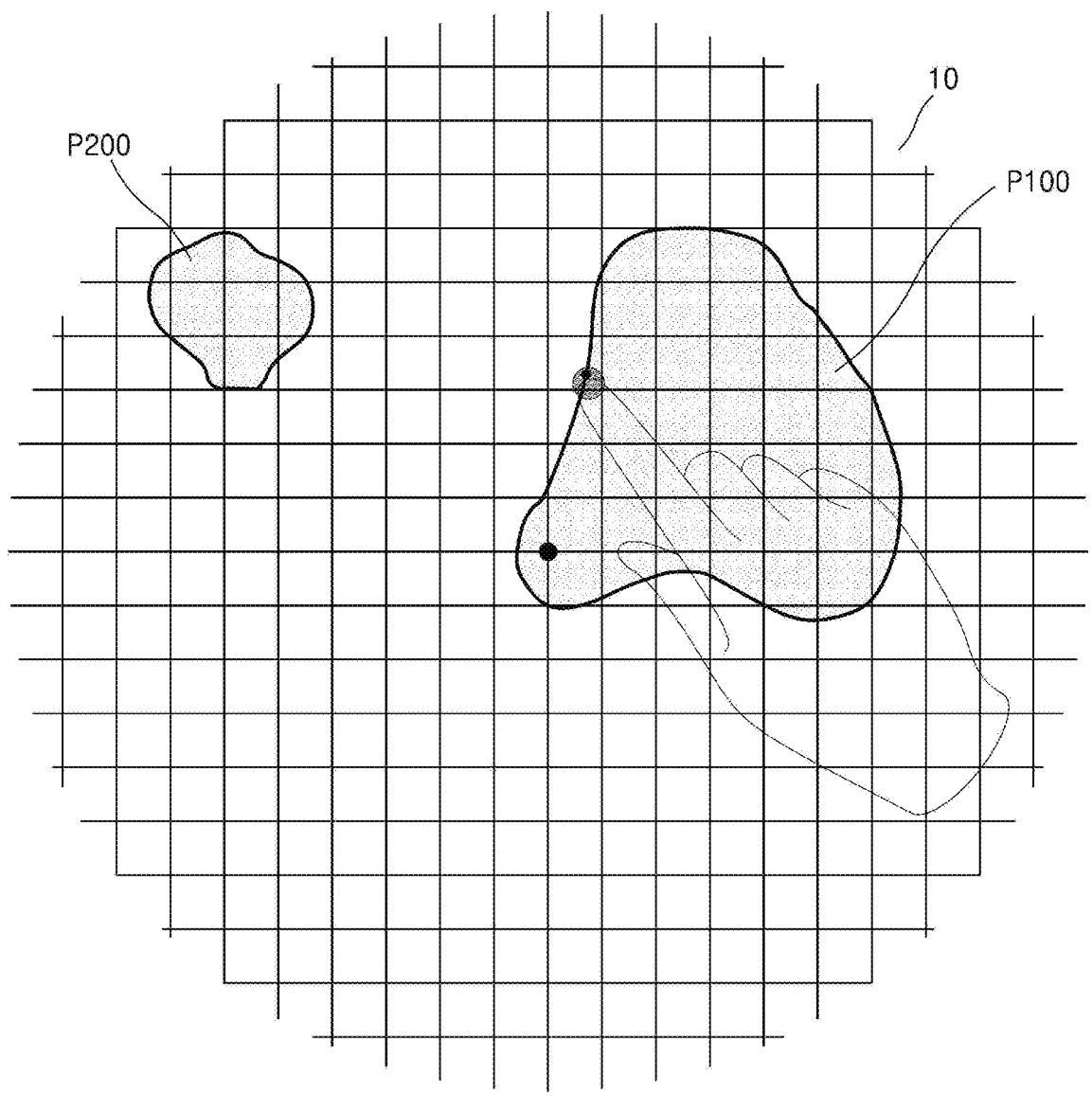
FIG. 3 illustrates a region displayed on a test chart by perceiving that metamorphopsia occurs by a user according to an embodiment of the present invention.

FIG. 2 illustrates an example of a test chart according to an embodiment of the present invention and FIG. 3 illustrates a region displayed on a test chart by perceiving that metamorphopsia occurs by a user according to an embodiment of the present invention.

Referring to FIGS. 2 and 3, the test chart 10 according to an embodiment of the present invention is a polygonal or circular grid and a user display input for displaying at least one metamorphopsia region for the test chart may be received through a user input unit of a metamorphopsia determining apparatus and the user display input may form a closed line on the test chart.

In addition, a center point of a predetermined size (e.g., 0.3 degrees, etc.) with respect to a visual angle of the user may be displayed on the grid-shaped test chart 10. Such a center point may be flickered, for example, by a size of 0.3 degrees of the visual angle in the middle of the test chart 10 to help the user watch the center.

The test chart 10 may be displayed as a black grid on a white background or as a white grid on a black background.

The size of a display unit according to an embodiment of the present invention may be, for example, 24 inches and a resolution may be full HD (1920×1080), and a distance up to the user (e.g., a testee or a patient) may be 50 cm, but are not particularly limited to the aforementioned numerical values. In other words, an electronic device capable of displaying the test chart may be the display unit according to an embodiment of the present invention and a separation distance between the display unit for the test and the user may be variously predetermined according to an age of the user, etc.

Figure 4:
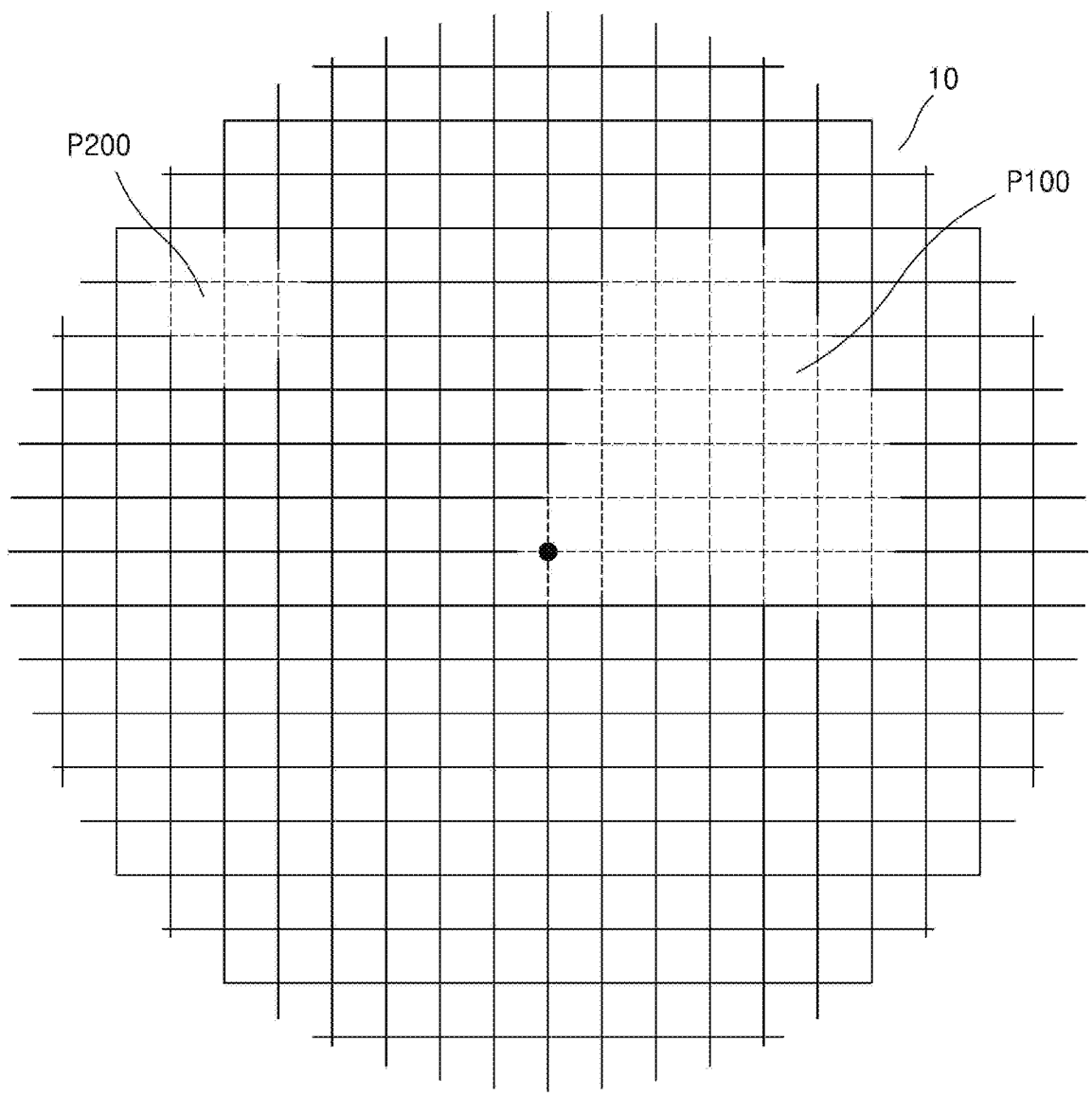
FIG. 4 illustrates a test chart including all regions where distances of points are adjusted by user's selection according to an embodiment of the present invention.

FIG. 4 illustrates a test chart including all regions where distances of points are adjusted by user's selection according to an embodiment of the present invention.

In the case of a patient with the metamorphopsia, a region in which the distances of the points are adjusted by performing the test according to an embodiment of the present invention may be shown on the test chart 10 as illustrated in FIG. 4.

Figure 5:
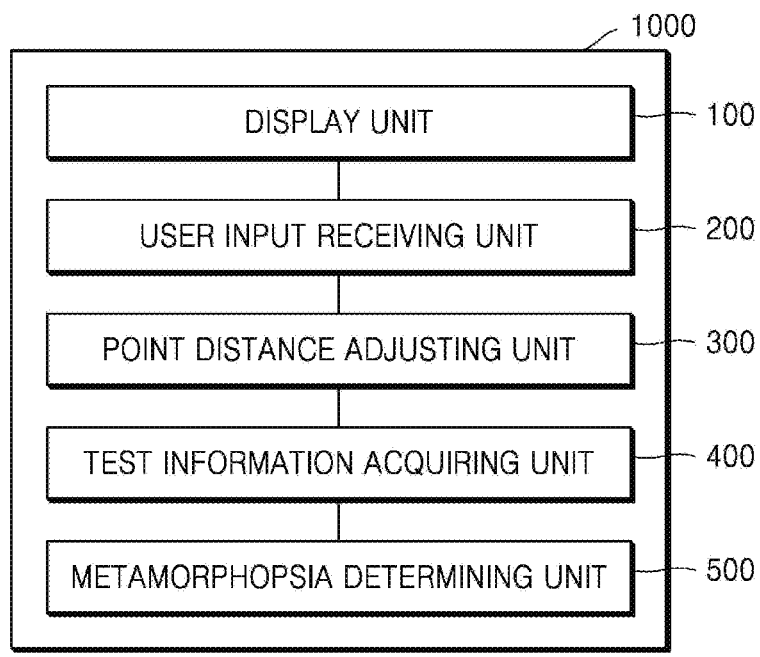
FIG. 5 is a block diagram illustrating an apparatus for determining metamorphopsia based on user interaction according to an embodiment of the present invention.

FIG. 5 is a block diagram illustrating an apparatus for determining metamorphopsia based on user interaction according to an embodiment of the present invention.

Further, an apparatus 1000 for determining metamorphopsia based on user interaction according to an embodiment of the present invention may include a display unit 100 for displaying a test chart to a user, a user input receiving unit 200 receiving a user display input for displaying at least one metamorphopsia region with respect to the test chart displayed through the display unit, a point distance adjusting unit 300 for adjusting distances of a plurality of points within at least one metamorphopsia region displayed based on the user display input received through the user input receiving unit by a point distance adjustment signal applied from the user, a test information acquiring unit 400 for acquiring distance values of a plurality of points within at least one metamorphopsia region and an area value of the metamorphopsia region when it is selected that the metamorphopsia is not perceived by the user, and a metamorphopsia determining unit 500 repeatedly performing previous steps when a user input that the metamorphopsia region still exists in a display part other than at least one metamorphopsia region displayed is received by the user and determining the metamorphopsia of the user based on the distance values of the points and the area value acquired by the test information acquiring unit when the metamorphopsia region does not exist on the test chart any longer.

Figure 6:
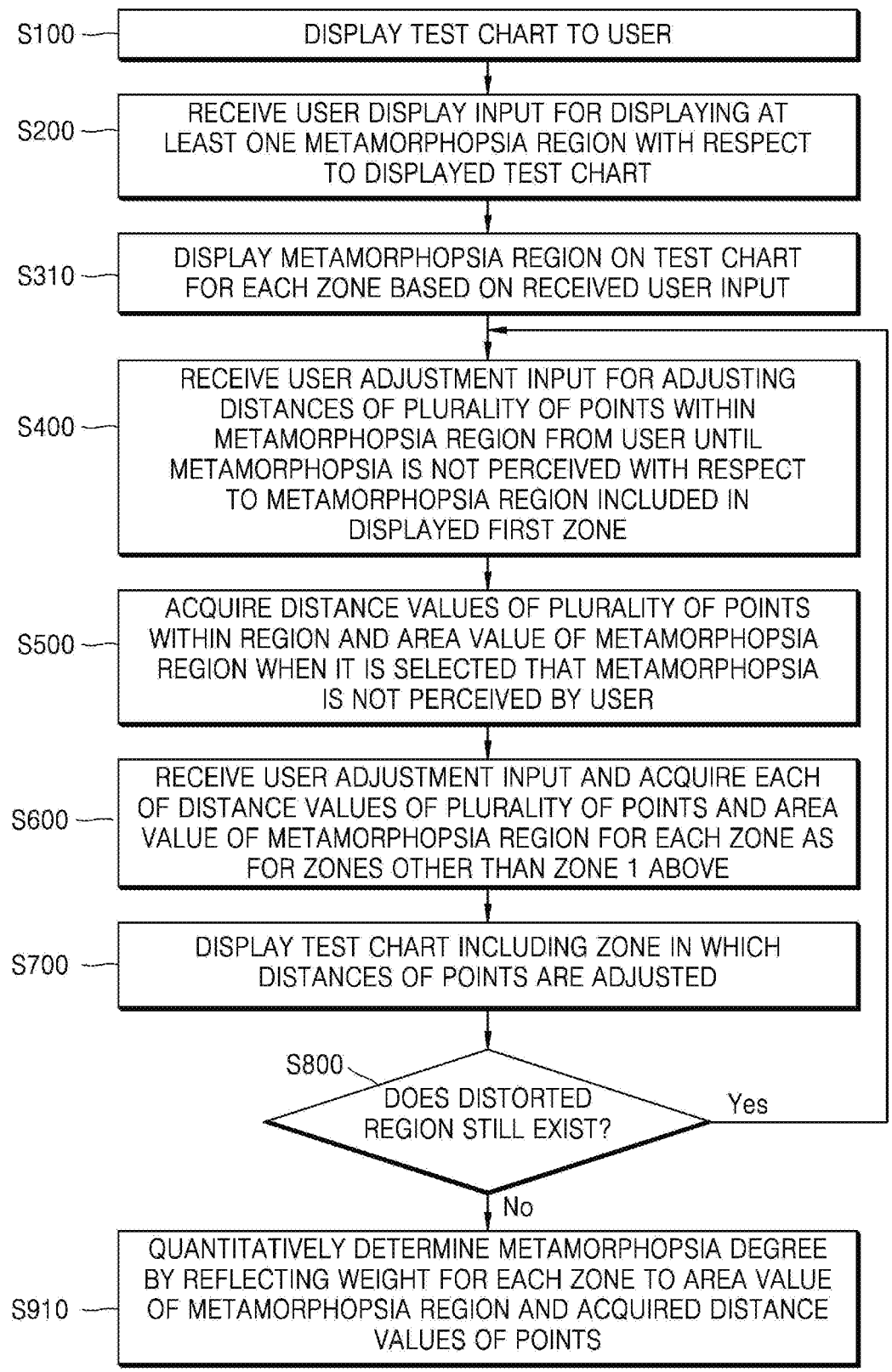
FIG. 6 is a flowchart illustrating a method for determining metamorphopsia using a point distance and an area for each zone based on user interaction according to another embodiment of the present invention.

FIG. 6 is a flowchart illustrating a method for determining metamorphopsia using a point distance and an area for each zone based on user interaction according to another embodiment of the present invention.

A method for determining metamorphopsia based on user interaction according to an embodiment of the present invention may include displaying a test chart for a user (S100), receiving a user display input for displaying at least one region (referred to as a metamorphopsia region) where the metamorphopsia is perceived with respect to the displayed test chart (S200), displaying a metamorphopsia region on the test chart for each zone based on the received user display input (S310), receiving a user adjustment input for adjusting distances of a plurality of points until the metamorphopsia is not perceived with respect to the metamorphopsia region included in a displayed first zone (S400), acquiring distance values of the plurality of points within the region and an area value of the metamorphopsia region when it is selected by the user that the metamorphopsia is not perceived by adjusting the distances of the points (S500), receiving the user adjustment input and acquiring each of the distance values of the plurality of points and the area value of the metamorphopsia region for each zone as the same procedure for zones other than Zone 1 above (S600), displaying the test chart including the zone in which the distances of the points are adjusted (S700), repeatedly performing previous steps when a user input that the metamorphopsia region still exists is received by the user (S800), and determining the metamorphopsia as a quantitative value to which a weight for each zone is reflected based on the area value (range) of the metamorphopsia region and the acquired distance values (degree) of the points when the metamorphopsia region does not exist (S910).

Figure 7:
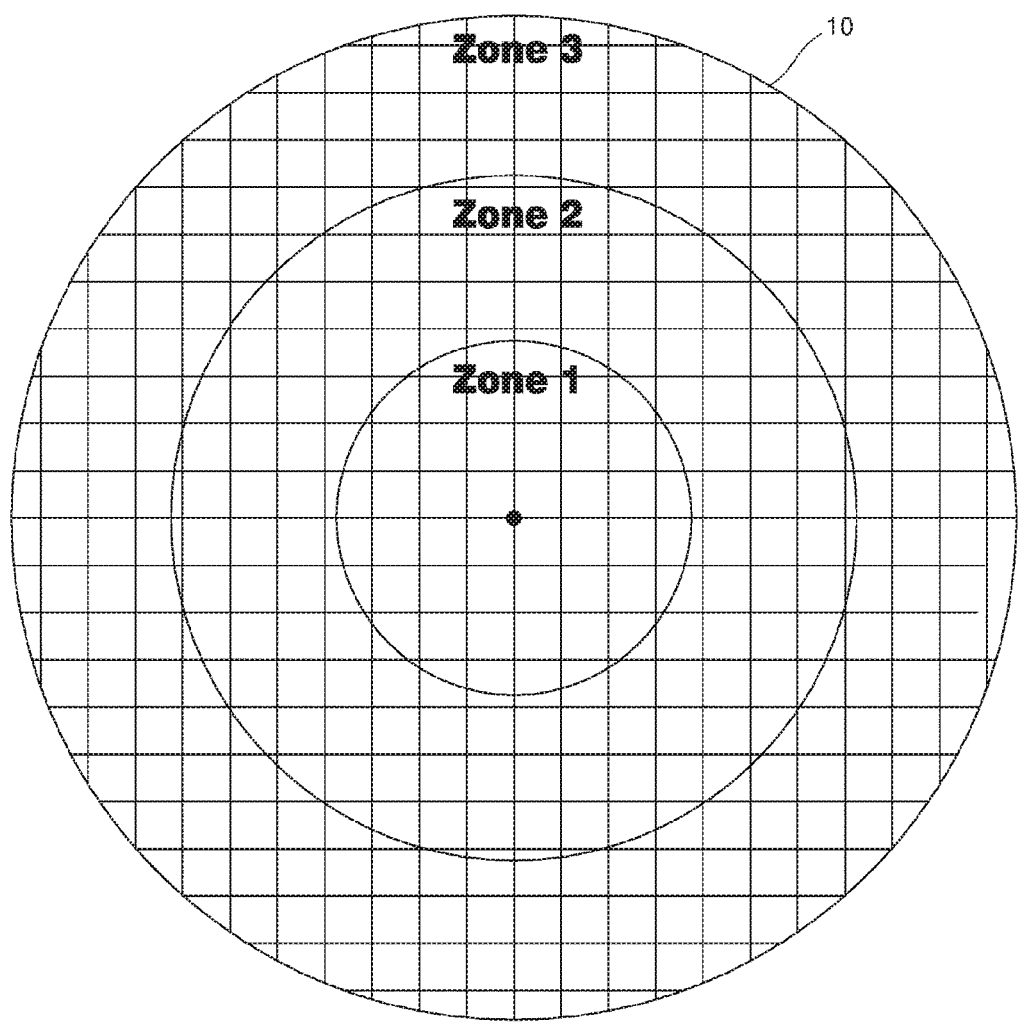
FIG. 7 illustrates at least one zone of a test chart according to an embodiment of the present invention.

FIG. 7 illustrates at least one zone of a test chart according to an embodiment of the present invention.

In the test chart 10 according to an embodiment of the present invention, a plurality of concentric circle-shaped zones having different sizes may exist around a center point and a concentric circle indicating each zone may have a diameter corresponding to a visual angle of the user from the center point.

The test chart according to an embodiment of the present invention may separately include a plurality of concentric circle zones and the zone may be pre-divided into virtual concentric regions corresponding to visual angles of 5 degrees (e.g., 4.37 cm), 15 degrees (e.g., 13.17 cm), and 30 degrees (e.g., 26.8 cm) around a black center point (e.g., 2.6 mm) of the center. Interiors of respective zones (circles) may be referred to as Zone 1 (e.g., in the case of the visual angle of 5 degrees), Zone 2 (e.g., in the case of a visual angle of 5 to 15 degrees), and Zone 3 (e.g., in the case of a visual angle of 15 to 30 degrees). The aforementioned numerical values are just used for description and the numerical values are not particularly limited thereto. In other words, the numerical values may be classified into a case where Zone 1 has a visual angle of 10 degrees, a case where Zone 2 has a visual angle of 20 degrees, etc.

According to an embodiment of the present invention, actually, in the test chart displayed through the display unit, only a straight line (e.g., a line width of 0.87 mm, etc.) configured by horizontal and vertical grids may be displayed so that the concentric circle is not seen. For example, the distance between the straight lines may be 8.7 mm, but the aforementioned numerical values are just used for description and the numerical values are not particularly limited thereto.

According to the method for determining metamorphopsia based on user interaction provided as an embodiment of the present invention, when personal information of the user is inputted, the test chart for the test may be displayed through the display unit. The personal information of the user may include information including a name, an age, gender, physical information including vision, and the like, a test history, a disease history, and the like of the user.

The metamorphopsia test may be individually performed with respect to a right eye or a left eye. Further, in the case of the determination of the metamorphopsia, the metamorphopsia may be individually determined for each eye just after testing each eye and determined for both eyes in combination.

Referring to FIG. 3, the user display input for displaying at least one metamorphopsia region for the displayed test chart 10 may be received through the user input receiving unit 200. The user input receiving unit 200 may be an electronic device such as a keyboard, a mouse, a joystick, a jog shuttle, an electronic pencil, or the like or a touch pad capable of receiving an input by touching or dragging an index finger of the user. For example, the user may directly display a region in which the metamorphopsia is seen (dicided) to occur on a screen of the display unit in which the test chart 10 is displayed while moving a display point (e.g., a 2.6-mm red point which is flickered) by touching the display unit of FIG. 3 while looking at the test chart 10. In other words, the user may display a portion of a line seen to be warped among a plurality of lines of the test chart 10 directly on the screen of the display unit. In the related art, since a test chart in which a predetermined fixed form (pattern) was printed was used before manufacturing, it was impossible to accurately determine both a metamorphopsia incidence portion of the user and an area thereof at the same time.

In the example described above, the user may display the metamorphopsia region while keeping a pressing state of a left click first once through the user input receiving unit 200 such as the mouse, etc., and then, continuing a free curve from a click start point. Further, the user may directly display the metamorphopsia region with the free curve on a touch pad type display by using a finger (e.g., index finger, etc.) thereof. While the free curve is generated, contours may be displayed on the display so that the user may determine a current state of contours drawn directly by the user. When the display of the metamorphopsia region does not form the closed line by the user, a message "Draw with the closed line again." may be displayed through the display unit. Further, before starting the test, a message "Display the region seen to be warped in the test chart with the closed line." may be displayed through the display unit.

Figure 8:
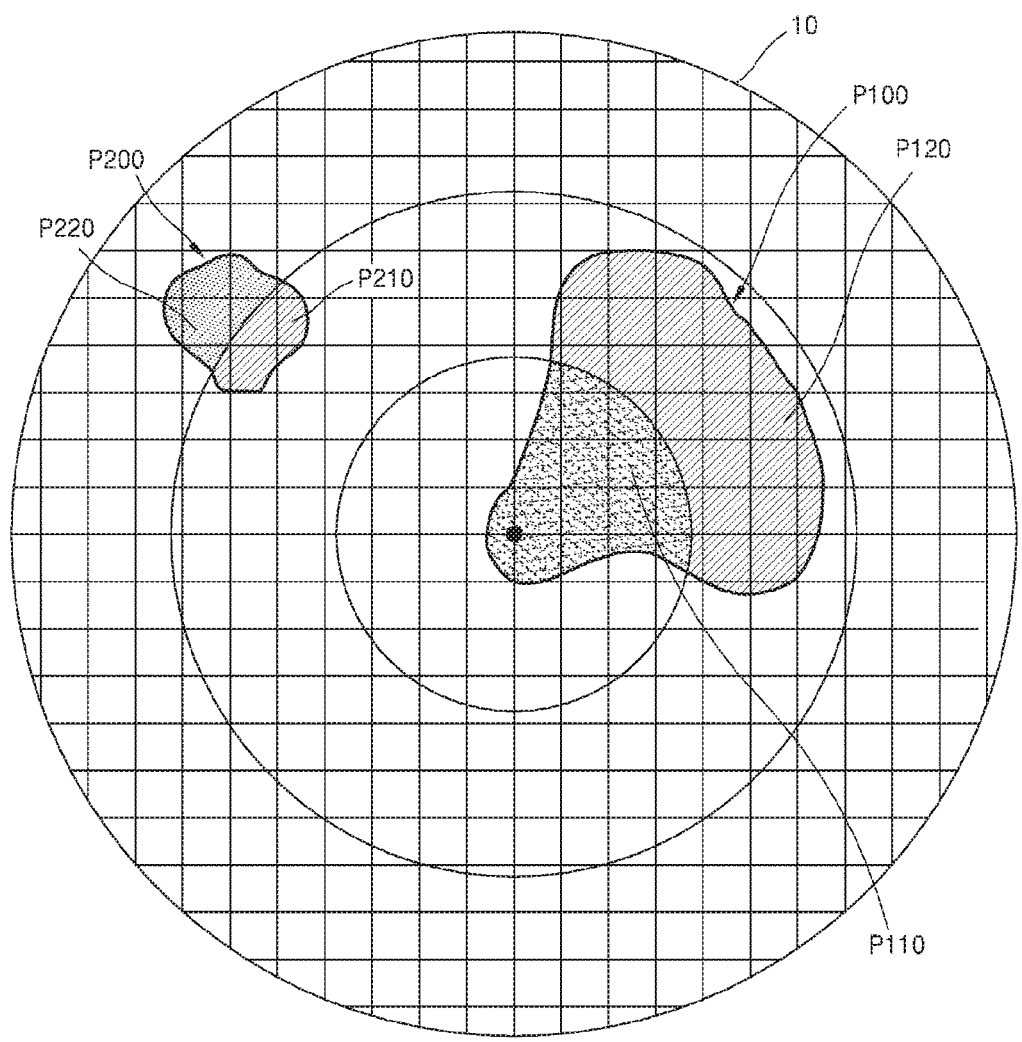
FIG. 8 illustrates a segmentation for each zone of a region indicated as having metamorphopsia according to an embodiment of the present invention.
Figure 9:
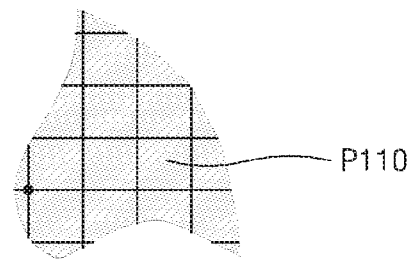
FIG. 9 illustrates a region in which metamorphopsia is perceived in a center zone (first zone) for each zone according to an embodiment of the present invention.
Figure 10:
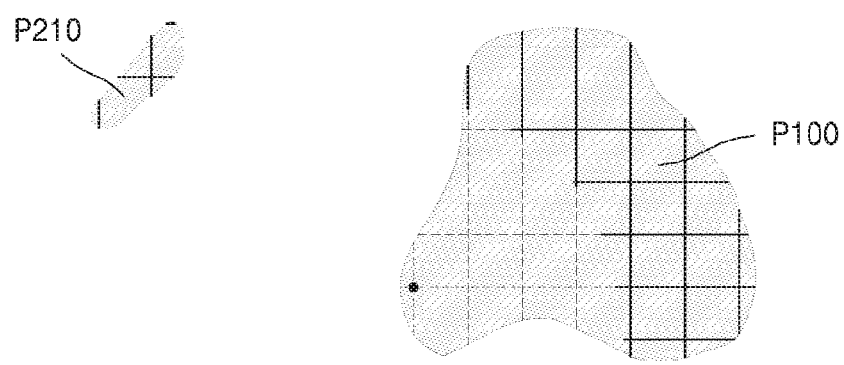
FIG. 10 illustrates a state immediately before a user adjusts distances of points of a peripheral zone (second zone) in a state in which distances of points are adjusted so that metamorphopsia at a center zone is not recognized according to an embodiment of the present invention.

FIG. 8 illustrates a segmentation for each zone of a metamorphopsia region according to an embodiment of the present invention, FIG. 9 illustrates a region for each zone according to an embodiment of the present invention, and FIG. 10 illustrates a segmentation for each zone including a region in which distances of points are adjusted according to an embodiment of the present invention.

According to an embodiment of the present invention, when there are multiple regions (e.g., the metamorphopsia region) seen to be warped in the test chart 10, the user may display all of the corresponding regions.

When all inputs for displaying the metamorphopsia region are received from the user, the metamorphopsia region of the test chart 10 may be displayed for each zone. Referring to FIG. 9, only a part P110 of a first metamorphopsia region P100, which is included in Zone 1 may be displayed through the display unit. In other words, a boundary line and a peripheral grid may not be displayed and the size of the grid (e.g., a plurality of lines) may be displayed equally.

Further, according to an embodiment of the present invention, the distances of the plurality of points increase or decrease based on the received user adjustment input and the distances of the plurality of points are fixed according to selection of an absence time of the metamorphopsia in the region by the user and the area value of the metamorphopsia region and the distance values of the plurality of points at the absence time of the metamorphopsia may be acquired.

A message such as "Focus on the center point, lower a mouse wheel, and increase a dotted line distance until the line does not look bent.", etc., may be displayed through the display unit. The user may adjust the distances of the points by using the user input receiving unit 200. For example, when the mouse wheel is lowered, the distances may gradually increase from a plurality of dotted lines (e.g., a straight line) constituting the grid in the form of the points and when the mouse wheel is raised, the distances may gradually decrease. Of course, an operation condition of the user input receiving unit 200 may be pre-configured so as to operate in an opposite manner thereto. In other words, as the user operates the mouse wheel, the distance of the grids may be adjusted from 0.2 degrees to 2.0 degrees. Here, 0.1 degree may be referred to as a case where the distance between the points is 0.87 mm.

When the distances of the points are increasingly widened between horizontal and vertical and then, it is selected by the user that there is no region (e.g., a part where the metamorphopsia is perceived) seen to be warped, the distance (e.g., M-score) values of the points and the area value of Zone 1 may be acquired. The acquired distance and area value may be stored in a storage unit provided in the apparatus 1000 or a database which may be connected to the apparatus 1000 in real time.

According to an embodiment of the present invention, in a state where a plurality of points of a fixed distance at the time selected by the user for the metamorphopsia region included in Zone 1 are displayed together with a plurality of points in the metamorphopsia region included in Zone 2, the distances of the plurality of points in the metamorphopsia region included in Zone 2 increase or decrease based on the received user adjustment input and the distances of the plurality of points in Zone 2 are fixed by the selection of the absence time of the metamorphopsia in the region within Zone 2 by the user, and the area value of the metamorphopsia region in Zone 2 and the distance values of the plurality of points in Zone 2 at the absence time of the metamorphopsia may be acquired.

When the aforementioned process is completed, the metamorphopsia region in Zone 2 may be displayed while a point distance last displayed in Zone 1 is maintained as it is through the display unit as illustrated in FIG. 10. In other words, in a state where the watch point of the center and dotted lines in which it is determined that there is no metamorphopsia in Zone 1 set by the user in the above process are shown, only a solid line of a metamorphopsia region portion (e.g., A-2 (P120) and B-2 (P210)) in Zone 2 may be displayed and the contour of the test chart 10 and other grids may not be displayed not to be seen.

For the metamorphopsia region portion (e.g., A-2 (P120) and B-2 (P210)) in Zone 2, the user may be allowed to adjust the distances of the points constituting the line similarly to the aforementioned scheme. That is, when the point distance is increasingly widened between the horizontal and the vertical and then, there is no region seen to be warped, the user may apply an input for selecting that the metamorphopsia is not perceived to the user input receiving unit. When it is selected by the user that the metamorphopsia is not perceived, the distance value of the plurality of points in the region in Zone 2 and the area value may be acquired and the acquired distance value and area value may be stored in the storage unit provided in the apparatus 1000 or the database which may be connected to the apparatus 1000 in real time.

By the same scheme as above, the distances of the points of the metamorphopsia region may be adjusted and the distance values of the plurality of points and the area value may be acquired with respect to a remaining zone (e.g., Zone 3, etc.) of the test chart 10. In other words, according to an embodiment of the present invention, in a state where the plurality of points of the fixed distance in Zone 1 and the plurality of points of the fixed distance in Zone 2 are displayed together with the plurality of points in the metamorphopsia region included in Zone 3, the distances of the plurality of points in the metamorphopsia region included in Zone 3 increase or decrease based on the received user adjustment input and the distances of the plurality of points in Zone 3 are fixed by the selection of the absence time of the metamorphopsia in the region within Zone 3 by the user, and the area value of the metamorphopsia region in Zone 3 and the distance values of the plurality of points in Zone 3 at the absence time of the metamorphopsia may be acquired. After the distance value and the area value of the plurality of points for all zones of the test chart 10 are obtained, the test chart 10 including the zone where the distances of the points are adjusted may be displayed as illustrated in FIG. 4. With respect to the displayed test chart 10, it may be determined by the user whether the metamorphopsia region still exists. In other words, when the user input that the region where the metamorphopsia is perceived by the user still exists is received, the previous steps may be repeatedly performed and when the metamorphopsia is not perceived any longer, the metamorphopsia of the user may be quantitatively determined based on the acquired distance values of the points and the area value.

The test chart 10 including the zone where the distances of the points are adjusted may be displayed from the display unit together with a message such as "Is there a region seen to be warped?", etc. The user may watch and determine whether there is still the region (e.g., the metamorphopsia region) seen to be warped in the test chart 10 while looking at the watch point at the center of the test chart 10 and represent a determination result through the user input receiving unit. That is, the user may represent the determination result by clicking either "present" or "not present" displayed from the display unit.

When the user input that the metamorphopsia region still exists is received by the user, the user may be allowed to additionally display the metamorphopsia region by activating a mouse pointer. In such a case, in a current state in which the point distance confirmed through the aforementioned process is expressed, the metamorphopsia region is displayed. In other words, the user displays the closed line to show the grid only with respect to a recent new displayed range and adjust the distances of the points through scrolling of a mouse wheel as described above. Further, when a newly displayed closed line extends over two or more zones, the closed lines are discriminated to perform the test (e.g., adjustment of the point distance, etc.) similarly to the aforementioned scheme. Such a process may be repeatedly performed until there is no region seen to be warped in the test chart 10 including the zone where the distances of the points are adjusted.

Thereafter, when it is perceived by the user that there is no metamorphopsia region, the metamorphopsia of one eye of the user may be quantitatively determined by reflecting the weight for each metamorphopsia zone based on the area value of the metamorphopsia region and the acquired distance value of the points. Further, the test may be performed even with respect to an opposite eye in the same process.

The determination of the metamorphopsia according to an embodiment of the present invention may be performed by the following scheme.

When a total length of the solid line in the first test chart 10 to which no operation is applied by the user is 100, the sum of lengths of an empty space between the points in a portion represented by dotted lines in each zone where the distances of the points are adjusted by the user is subtracted from the total length to acquire a metamorphopsia degree value (score). The acquired metamorphopsia degree value may become one element of determination of the metamorphopsia.

Further, according to an embodiment of the present invention, the weight is differently applied for each zone to correct the total sum of the distances of the points and the weight may be assigned to be high as being closer to the center of the test chart 10. For example, the weight for each zone may be preset as follows.

(i) Zone 1 (within 5 degrees): 3.29
(ii) Zone 2 (5 to 15 degrees): 0.79
(iii) Zone 3 (15 to 30 degrees): 0.45

Further, such a weight may be changed and set according to a test condition (e.g., the age, the vision, presence or absence of an eye disease history, etc. of the patient).

For example, when the sum of the length of the empty space between the points in the portion represented by the dotted line in each zone is 4.3 in (i), 2.1 (ii), and 0.5 in (iii), the metamorphopsia degree value may be acquired as 100−(4.3×3.29)−(2.1×0.79)−(0.5×0.45)=84.149.

In other words, according to an embodiment of the present invention, the degree of the metamorphopsia may be quantified and expressed quantitatively. Therefore, a medical person (for example, a clinician, a nurse, a test assistant, or the like) who inspects a testee or the patient may diagnose (determine) the range and degree of the metamorphopsia more quickly and accurately than the related art based on quantitatively expressed information.

An apparatus 100 for determining metamorphopsia based on user interaction according to another embodiment of the present invention may include a display unit 100 for displaying a test chart to a user, a user input receiving unit 200 receiving a user display input for displaying at least one metamorphopsia region for the test chart displayed through the display unit 100, a test information acquiring unit 400 for acquiring distance values of a plurality of points in a region and an area value of the metamorphopsia region when the metamorphopsia region of the test chart is displayed for each zone through the display unit 100 based on the user display input received through the user input receiving unit 200, a user adjustment input for adjusting the distances of the plurality of points is received through the user input receiving unit 200 until the metamorphopsia is not perceived with respect to a metamorphopsia region included in displayed Zone 1, and it is selected that the metamorphopsia is not perceived by a user, and a metamorphopsia determining unit 500 for quantitatively expressing and determining a range and a degree (e.g., a grade or a representative value) of the metamorphopsia by reflecting a weight for each zone based on the acquired distance of the points and the acquired area value when the user adjustment input is received even with respect to another zone other than Zone 1, each of a distance value of the plurality of points for each zone and an area value of the metamorphopsia region is acquired, a test chart including a zone where the distances of the points are adjusted is displayed through the display unit 100, and a user input that the metamorphopsia region still exists is received by a user through the user input receiving unit 200, the distances of the plurality of points in the region for each zone are repeatedly adjusted, and the metamorphopsia region does not exist. Further, as illustrated in FIG. 5, the apparatus 1000 for determining metamorphopsia based on user interaction may include a point distance adjusting unit 300.

According to an embodiment of the present invention, a description of a method for driving the apparatus 1000 for determining metamorphopsia based on user interaction may be provided to the user before the test. That is to say, as a tutorial, a metamorphopsia test process according to an embodiment of the present invention may be played as pre-made multimedia contents such as a moving picture, etc., and provided to the user through the display unit.

The method and the apparatus for determining metamorphopsia based on user interaction according to an embodiment of the present invention may be similarly applied even under a home healthcare environment. In other words, the patient may perform a process as the aforementioned metamorphopsia determining method in a home, etc., by using a retaining device (e.g., a personal terminal such as a mobile phone, a tablet PC, etc.) thereof and verify a performing result through the retaining device of the patient on the spot. Further, the performing result acquired through the aforementioned process may be provided to a medical institute such as a hospital, etc., from the retaining device of the patient through a wired or wireless network.

The contents for the methods described above may be applied to the apparatus according to an embodiment of the present invention. Accordingly, described contents regarding the apparatus, which are the same as the contents regarding the aforementioned method are omitted.

An embodiment of the present invention may be implemented even in the form of a recording medium including a command executable by a computer such as a program module executed by the computer. A computer readable medium may be a predetermined available medium accessible by the computer or includes all of volatile and non-volatile media and removable and irremovable media. Further, the computer readable medium may include all computer storage media. The computer storage medium includes all of the volatile and non-volatile and removable and irremovable media, and an arbitrary information transfer medium implemented by a predetermined method or technology for storing information such as a computer readable command, a data structure, a program module, or other data.

The aforementioned description of the present invention is used for exemplification, and it can be understood by those skilled in the art that the present invention can be easily modified in other detailed forms without changing the technical spirit or requisite features of the present invention. Therefore, it should be appreciated that the aforementioned embodiments are illustrative in all aspects and are not restricted. For example, respective constituent elements described as single types can be distributed and implemented, and similarly, constituent elements described to be distributed can also be implemented in a coupled form.

The scope of the present invention is represented by claims to be described below rather than the detailed description, and it is to be interpreted that the meaning and scope of the claims and all the changes or modified forms derived from the equivalents thereof come within the scope of the present invention.

What is claimed is:

1. A method for determining metamorphopsia based on user interaction, the method comprising:
   (a) displaying a test chart to a user;
   (b) receiving a user display input for displaying at least one metamorphopsia region with respect to the displayed test chart;
   (c) displaying the test chart, while adjusting distances of a plurality of points in the at least one metamorphopsia region displayed based on the received user display input by a point distance adjustment signal applied from the user;
   (d) responsive to receiving a user input that the at least one metamorphopsia region is still perceived by the user in the at least one metamorphopsia region that is displayed, repeating steps (a) to (c); and
   (e) responsive to receiving a user input that the at least one metamorphopsia region is no longer perceived by the user in the at least one metamorphopsia region that is displayed, acquiring a distance value of the plurality of points in the at least one metamorphopsia region and an area value of the at least one metamorphopsia region, and determining a metamorphopsia degree of the user based on the acquired distance value of the plurality of points and the area value,
   wherein the acquired distance value of the plurality of points and the area value are weighted based on a distance of the at least one metamorphopsia region from a center point of the test chart.

2. The method of claim 1, wherein the test chart is a polygonal or circular grid, and
   wherein the user display input for displaying the at least one metamorphopsia region for the test chart is received through a user input unit of a metamorphopsia determining apparatus and the user display input forms a closed line.

3. The method of claim 1, wherein the center point is displayed on the test chart with a predetermined size, the test chart having a grid shape with respect to a visual angle of the user.

4. The method of claim 2, wherein the test chart is displayed as a black grid on a white background or as a white grid on a black background.

5. The method of claim 1, wherein the metamorphopsia degree of the user is determined by a multiplication result value of the acquired distance value of the plurality of points and the area value.

6. The method of claim 5, wherein the metamorphopsia degree of the user is determined by a value obtained by subtracting the multiplication result value from a measurement reference value.

7. The method of claim 1, wherein the metamorphopsia degree of the user is determined by a multiplication result value of a ratio value of the acquired distance of the plurality of points to a distance between respective lines and the acquired area value in the test chart having a grid shape.

8. An apparatus for determining metamorphopsia based on user interaction, the apparatus comprising:
   a display unit for displaying a test chart to a user;
   a user input receiving unit for receiving a user display input for displaying at least one metamorphopsia region with respect to the test chart displayed through the display unit;
   a point distance adjusting unit for adjusting distances of a plurality of points in the at least one metamorphopsia region displayed based on the user display input received by the user input receiving unit by a point distance adjustment signal applied from the user;
   a repetition determining unit for repeatedly performing operations of the display unit, the user input receiving unit, and the point distance adjusting unit in response to receiving a user input that the at least one metamorphopsia region is still perceived by the user in the at least one metamorphopsia region displayed;
   a test information acquiring unit for acquiring distance values of the plurality of points within the at least one metamorphopsia region and an area value of the at least one metamorphopsia region in response to receiving a user input that the at least one metamorphopsia region is no longer perceived by the user; and a metamorphopsia determining unit for determining a metamorphopsia degree of the user based on the distance values of the plurality of points and the area value acquired by the test information acquiring unit in response to receiving the user input that the at least one metamorphopsia region is no longer perceived by the user on the test chart, wherein the metamorphopsia determining unit is configured to weight the distance values of the plurality of points and the area value acquired by the test information acquiring unit based on a distance of the at least one metamorphopsia region from a center point of the test chart.

9. A method for determining metamorphopsia based on user interaction, the method comprising:

displaying a test chart to a user comprising a plurality of zones, wherein the plurality of zones comprise a plurality of concentric circle-shaped zones having different sizes disposed around a center point in the test chart, and wherein a concentric circle defining each of the plurality of zones has a diameter corresponding to a visual angle of the user from the center point;

receiving a user display input for displaying at least one metamorphopsia region with respect to the displayed test chart;

displaying the at least one metamorphopsia region on the test chart for each of the plurality of zones based on the received user display input;

receiving a user adjustment input for adjusting distances of a plurality of points within the at least one metamorphopsia region from the user until the at least one metamorphopsia region is no longer perceived by the user with respect to portions of the at least one metamorphopsia region included in a displayed first zone of the plurality of zones;

acquiring distance values of a plurality of points within the first zone and an area value of the at least one metamorphopsia region within the first zone in response to determining that the at least one metamorphopsia region within the first zone is no longer perceived by the user;

receiving the user adjustment input for adjusting distances of a plurality of points within the at least one metamorphopsia region for each additional zone other than the first zone;

repeatedly performing the receiving of the user adjustment input for adjusting distances of the plurality of points within each of the additional zones from the user until portions of the at least one metamorphopsia region in each of the additional zones are no longer perceived by the user;

acquiring distance values of the plurality of points within each of the additional zones and area values of the portions of the at least one metamorphopsia region in each of the additional zones in response to determining that the at least one metamorphopsia region is no longer perceived by the user in each of the additional zones; and determining the metamorphopsia of the user based on the acquired distance values of the plurality of points and the area values from the first zone and from each of the additional zones.

10. The method of claim 9, wherein the distances of the plurality of points increase or decrease based on the received user adjustment input, and wherein the distances of the plurality of points are fixed according to selection of an absence time of the at least one metamorphopsia region by the user and the area value of the at least one metamorphopsia region, and the distance values of the plurality of points at the absence time of the at least one metamorphopsia region are acquired.

11. The method of claim 10, wherein in a state where the plurality of points of a fixed distance at the absence time selected by the user for the at least one metamorphopsia region included in the first zone is displayed together with the plurality of points in the at least one metamorphopsia region included in a second zone of the plurality of zones, the distances of the plurality of points in the at least one metamorphopsia region included in the second zone increase or decrease based on the received user adjustment input and the distances of the plurality of points in the second zone are fixed by the selection of the absence time of the at least one metamorphopsia region within the second zone by the user, and the area value of the at least one metamorphopsia region in the second zone and the distance values of the plurality of points in the second zone at the absence time of the at least one metamorphopsia region are acquired.

12. The method of claim 11, wherein in a state where the plurality of points of the fixed distance in the first zone and the plurality of points of the fixed distance in the second zone are displayed together with the plurality of points in the at least one metamorphopsia region included in a third zone, the distances of the plurality of points in the metamorphopsia region included in the third zone increase or decrease based on the received user adjustment input and the distances of the plurality of points in the third zone are fixed by the selection of the absence time of the at least one metamorphopsia region within the third zone by the user, and the area value of the metamorphopsia region in the third zone and the distance values of the plurality of points in the third zone at the absence time of the at least one metamorphopsia region are acquired.

13. The method of claim 12, wherein the entirety of the test chart including the plurality of points of the fixed distance is displayed for each zone, and in response to the at least one metamorphopsia region being no longer perceived in the test chart by the user, a degree of the metamorphopsia of the user is determined based on the distance values of the plurality of points and the area value which are acquired for each zone.

14. The method of claim 13, wherein the degree of the metamorphopsia of the user is determined based on a difference between a total length of a solid line included in the test chart before a metamorphopsia test for the user and a total sum of the distances of the plurality of points for each zone.

15. The method of claim 14, wherein a weight is differently applied for each zone to correct the total sum of the distances of the plurality of points and the weight is assigned to be high as being closer to the center point of the test chart.

16. An apparatus for determining metamorphopsia based on user interaction, the apparatus comprising:

a display unit for displaying a test chart to a user comprising a plurality of zones;

a user input receiving unit receiving a user display input for displaying at least one metamorphopsia region with respect to the test chart displayed through the display unit and a user adjustment input;

a point distance adjusting unit for adjusting distances of a plurality of points within a first zone of the plurality of zones based on the user adjustment input received from the user until the at least one metamorphopsia region in the first zone is no longer perceived by the user;

a test information acquiring unit for acquiring distance values of the plurality of points in the first zone and an area value of the at least one metamorphopsia region of the first zone in response to determining that the at least one metamorphopsia region of the test chart is no longer perceived by the user in the first zone, the user input receiving unit further receiving the user adjustment input and the point distance adjustment unit further adjusting distances of a plurality of points of the at least one metamorphopsia region for each additional zone of the plurality of zones other than the first zone until the at least one metamorphopsia region in each of the additional zones is no longer perceived by the user, and the test information acquiring unit further acquiring distance values of the plurality of points within each of the additional zones and area values of the at least one metamorphopsia region of each of the additional zones in response to determining that the at least one metamorphopsia region is no longer perceived by the user in each of the additional zones; and a metamorphopsia determining unit quantitatively determining the metamorphopsia of the user based on the acquired distance values of the plurality of points and the area values from each of the plurality of zones and reflecting a different weight for each zone based on an area of the at least one metamorphopsia region and the acquired distance values of the plurality of points for each zone in response to determining that the at least one Metamorphopsia region is no longer perceived by the user in each of the plurality of zones.

17. A non-transitory computer readable recording medium having a program for implementing the method of claim 1, which is recorded therein.

18. The method of claim 1, wherein a weight of the acquired distance value of the plurality of points and the area value is increased as a location of the at least one metamorphopsia region is closer to the center point of the test chart.

19. The method of claim 1, wherein the test chart comprises a plurality of zones concentrically arranged around the center point of the test chart, and
wherein the acquired distance value of the plurality of points and the area value are weighted based on a location of the at least one metamorphopsia region within one of the plurality of zones.

20. The apparatus of claim 16, wherein the weight is differently applied for each of the plurality of zones to correct the acquired distance values of the plurality of points and the area values from each of the plurality of zones, and
wherein the weight for a particular zone of the plurality of zones is higher when the particular zone is closer to a center point of the test chart.

\* \* \* \* \*